United States Patent [19]
Johnson

[11] Patent Number: 5,016,649
[45] Date of Patent: May 21, 1991

[54] PROTECTIVE MASK

[76] Inventor: Joseph T. Johnson, 8028 Regency Park La., Charlotte, N.C. 28210

[21] Appl. No.: 419,502

[22] Filed: Oct. 10, 1989

[51] Int. Cl.$^5$ .............................................. A61F 13/12
[52] U.S. Cl. .................................. 128/859; 128/857; 128/917; 128/918
[58] Field of Search ............... 128/857, 859, 917, 918; 604/352

[56] References Cited

U.S. PATENT DOCUMENTS

| | | | |
|---|---|---|---|
| 1,296,946 | 3/1919 | Galiardo | 128/859 X |
| 1,297,842 | 3/1919 | Harllee | 128/857 X |
| 1,986,988 | 8/1934 | Treadweu | 128/857 |
| 2,276,612 | 3/1942 | Ellis | 128/857 |
| 3,135,962 | 6/1964 | Dunning | 128/857 X |
| 4,815,456 | 3/1989 | Rubin et al. | 604/352 X |
| 4,825,878 | 5/1989 | Kuntz et al. | 128/857 |

*Primary Examiner*—Robert A. Hafer
*Assistant Examiner*—Kevin G. Rooney
*Attorney, Agent, or Firm*—Rhodes, Coats & Bennett

[57] ABSTRACT

This invention relates to a protective mask, and more particularly to a protective mask usable during the act of oral sex or during the performance of mouth-to-mouth resuscitation to protect a wearer against infection with communicable diseases including viral diseases such as the human immune virus which leads to the development of acquired immune deficiency syndrome (AIDS). The mask is formed by an elongate, generally planar membrane of a tough film material having, when lying flat, a longitudinal axis and an outline configuration which is asymmetrical about that axis, the outline configuration having a lateral extension portion for extending downwardly and rearwardly over the chin of a wearer. The mask is securely wrapped in place over the lower face of a wearer while permitting free movement of the jaw, lips and tongue of the wearer and includes a flaccid pouch-like central portion.

3 Claims, 1 Drawing Sheet

PROTECTIVE MASK

FIELD AND BACKGROUND OF INVENTION

This invention relates to a protective mask, and more particularly to a protective mask usable in protecting a wearer against infection with communicable diseases including viral diseases such as the human immune virus which leads to the development of acquired immune deficiency syndrome (AIDS).

AIDS has become a communicated disease of substantial concern to many, specifically including emergency medical personnel and others who are exposed to blood and other body fluids of the public at large as well as those who may engage in consensual sexual activities particularly oral sex. Much emphasis has been given to preventative steps which can be taken to guard against infection with the human immune virus through consensual sexual activity, including advertisements promoting the use of condoms and the like. However, little emphasis has been given to other circumstances in which protection is at least equally needed.

At least two prior attempts have been made at providing protective masks which may possibly have some limited effectiveness Treadwell, in U.S. Pat. No. 1,986,988, proposes a two part applicator for mouth suction which extends over the immediate area of a wearer's mouth and provides a membrane and a separate cup which is capable of receiving fluids such as snake bite poison Rubin, in U.S. Pat. No. 4,815,456, proposes a one piece membrane similar in general size and configuration to that of Treadwell and having a central protuberant extension of the membrane for participants in oral sex.

Neither Treadwell nor Rubin provides an area of coverage of the face of a wearer which extends over more than the minimum area required to cover the lips. Thus both of these prior teachings leave substantial areas of the face of a wearer exposed and the wearer at risk. Further, due in part to the reduced area of coverage, both Treadwell and Rubin limit the freedom of movement of the jaw, lips and tongue of a wearer of their devices, undesirably limiting the activity in which a wearer might otherwise choose to engage.

Another example of a high risk activity is that of emergency personnel performing mouth-to-mouth resuscitation on unknown patients. In either of these activities (resuscitation or oral sex), free unrestricted use of the tongue, lips, and jaw are necessary, and to eliminate 90% of the disease-carrying micro-organisms is not sufficient.

BRIEF DESCRIPTION OF DISCLOSURE

With the foregoing discussion in mind, it is an object of this invention to provide an improved protective mask which is capable both of protecting the facial area of a wearer from undesirable exposure to infection carrying microorganisms. At the same time the mask permits unrestricted freedom of movement for the jaw, lips and tongue of a wearer. In realizing this object of the present invention, the present invention contemplates a protective mask which is formed of an elongate, generally planar membrane of a tough virus impermeable film material. The mask, when lying flat, includes a longitudinal axis and an outline configuration which is asymmetrical about said axis. The planar area is of such a width on either side of the axis as to cover, when worn, an area of the face extending from immediately beneath the nostrils to below the chin and jaw, and substantially all of the cheeks. The outlying configuration has a lateral extension portion for extending downwardly and rearwardly over the chin of wearer. To maintain the lateral extension in tight protective relationship to the area beneath the chin, ties which extend behind the head of the wearer are attached to the lateral extension for securing the mask in place.

Yet a further object of this invention is to protect a wearer of a mask in accordance with this invention while accommodating freedom of movement of the jaw, lips and tongue of the wearer. In realizing this object of the invention, the membrane further has a flaccid pouch-like central portion lying on said axis and generally medially of the length and width of said membrane for accommodating free movement of the tongue of a wearer. Finally it is an object of the present invention to provide emergency personnel with a one-way valve which may be used in conjunction with the mask to permit the passage of air from the rescuer to the patient, but which prevents the return flow of air in the reverse direction from the patient to the rescuer.

BRIEF DESCRIPTION OF DRAWINGS

Some of the objects of the invention having been stated, other objects will appear as the description proceeds, when taken in connection with the accompanying drawings, in which.

DETAILED DESCRIPTION OF INVENTION

Figures 1, 2, 3:
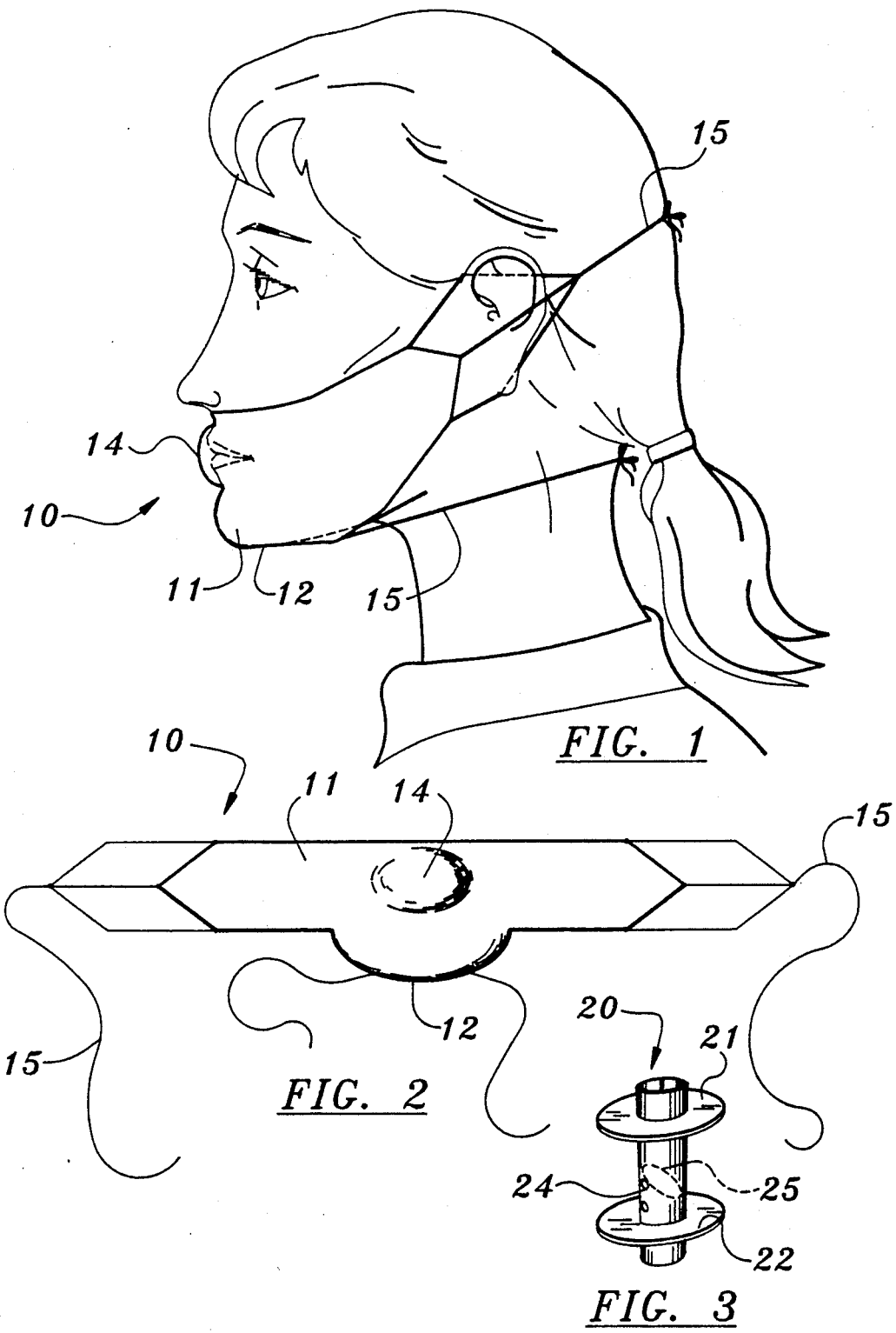
FIG. 1 is an elevation view showing the mask of this invention as worn by a wearer.
FIG. 2 is a plan view of the mask of FIG. 1 as laid out flat, illustrating the configuration of the mask which enables the facial coverage shown in FIG. 1.
FIG. 3 is a perspective view of an accessory useful with the mask of FIGS. 1 and 2 in accomplishing mouth to mouth resuscitation of a person who has stopped breathing.

While the present invention will be described more fully hereinafter with reference to the accompanying drawings, in which a preferred embodiment of the present invention is shown, it is to be understood at the outset of the description which follows that persons of skill in the appropriate arts may modify the invention here described while still achieving the favorable results of this invention. Accordingly, the description which follows is to be understood as being a broad, teaching disclosure directed to persons of skill in the appropriate arts, and not as limiting upon the present invention.

Referring now more particularly to the accompanying drawing, a mask as contemplated by this invention is show there in FIGS. 1 and 2 and indicated generally at 10. The mask is formed to protectively enclose an area of the face of a wearer extending from just below the nostrils to below the jaw and from cheek to cheek (FIG. 1). The mask 10 is formed by an elongate, generally planar membrane 11 of a virus impermeable tough film material and has, when lying flat (FIG. 2), a longitudinal axis and an outline configuration which is asymmetrical about that axis. The outline configuration defines a lateral extension portion 12 located lengthwise of the membrane 11 medially of the length thereof as measured along the longitudinal axis for extending downwardly and rearwardly over the chin of a wearer. The membrane 11 also has a flaccid pouch-like central portion 14 lying on the longitudinal axis and generally medially of the length and width of the membrane 11 for accommodating free movement of the tongue of a wearer. In order to affix the mask in place on the head of a wearer during use, means shown in the form of strings or other strands 15 are secured to end portions of the membrane and to the lateral extension portion 12 for securing the mask wrapped in place over the lower face of a wearer while permitting free movement of the jaw, lips and tongue of the wearer. As will be understood, it is preferable that the membrane 11 be formed of a virus impermeable material which is sufficiently tough to withstand, without bursting or opening a hole, the activity and movement in which a wearer may engage.

FIG. 3 illustrates an accessory useful with the mask of FIGS. 1 and 2 wherein a person wishes to provide mouth to mouth resuscitation to a non-breathing person while being protected against possible infection. The accessory is a breathing tube, indicated generally at 20, which may be positioned penetrating the membrane 11 and placed against the otherwise masked mouth of the rescuer and the unmasked mouth of the non-breather. The tube 20 has a central passageway and a pair of abutment members 21 and 22 which engage the masked and unmasked mouths and limit the proximity of the two persons. The central passageway has peripheral openings 24 and a check or one way valve member 25 which may be molded in place on formation of the tube 20, as by injection molding. The purpose of the valve member 25 is to permit air expelled from the masked person to pass through the passageway and into the mouth of the non-breathing person. The purpose of the peripheral openings 24 is to permit air exhaled by or expelled from the lungs of the non-breathing person to pass to the atmosphere without reaching the mouth of the masked person, such flow being blocked by the one way valve member 25.

As will be understood, in use with the membrane 11, the accessory tube 20 may permit a wearer to be exposed to some risk of infection through providing mouth to mouth resuscitation and yet will be a substantial improvement over the risk inherent in direct mouth to mouth contact.

In the drawings and specifications there has been set forth a preferred embodiment of the invention and, although specific terms are used, the description thus given uses terminology in a generic and descriptive sense only and not for purposes of limitation.

What is claimed is:

1. A protective device for emergency use by a rescuer in the administration of mouth-to-mouth resuscitation to a patient comprising: p1 (a) a protective mask comprising an elongate, generally planar membrane of a tough film material having, when lying flat, a longitudinal axis and an outline configuration which is asymmetrical about said axis, said membrane being of such a width on either side of said axis as to cover, when worn, are area of the face extending from immediately beneath the nostrils to below the chin and jaw, and substantially all of the cheeks, said outline configuration having a lateral extension portion which, when worn, extends downwardly over and rearwardly under the chin of a wearer, and means secured to end portions of said membrane and to said lateral extension portion for securing the mask wrapped in place over the lower face of a wearer while permitting free movement of the jaw, lips and tongue of the wearer;

(b) a breathing tube insertable through said membrane of said mask, said breathing tube including:
      (i) a tubular member forming a central passageway and having a rescuer end and a patient end;
      (ii) a valve means positioned within the tubular member for permitting the passage of fresh air from the rescuer to the patient but preventing passage of air in the reverse direction; and
      (iii) vent means in a wall of said tubular member between the valve means and the patient end of said tubular member for permitting passage of air leaving the patient's mouth of the atmosphere without reaching the mouth of the rescuer.

2. The protective device according to claim 1 wherein said tubular member further includes a pair of abutment disks surrounding said tubular member at spaced points therealong, a first one of said disks positioned adjacent the rescuer end of said tubular member and a second one of said disks positioned adjacent the patient end of said tubular member, said disks limiting the proximity of rescuer and patient.

3. The protective device according to claim 1 wherein said valve means is a one-way valve.

* * * * *